US012778927B2

(12) United States Patent
Hofland et al.

(10) Patent No.: US 12,778,927 B2
(45) Date of Patent: Nov. 3, 2026

(54) METHODS FOR PALMAR OR PLANTAR ADMINISTRATION OF PHARMACEUTICAL COMPOSITIONS

(71) Applicant: JOURNEY MEDICAL CORPORATION, Scottsdale, AZ (US)

(72) Inventors: Hans E.J. Hofland, Scottsdale, AZ (US); Janice S. Drew, Scottsdale, AZ (US)

(73) Assignee: JOURNEY MEDICAL CORPORATION, Scottsdale, AZ (US)

( * ) Notice: Subject to any disclaimer, the term of this patent is extended or adjusted under 35 U.S.C. 154(b) by 1059 days.

(21) Appl. No.: 17/774,850

(22) PCT Filed: Nov. 4, 2020

(86) PCT No.: PCT/US2020/058978
§ 371 (c)(1),
(2) Date: May 5, 2022

(87) PCT Pub. No.: WO2021/092090
PCT Pub. Date: May 14, 2021

(65) Prior Publication Data

US 2022/0401412 A1 Dec. 22, 2022

Related U.S. Application Data

(60) Provisional application No. 62/931,139, filed on Nov. 5, 2019.

(51) Int. Cl.

| | |
|---|---|
| ***A61K 31/4015*** | (2006.01) |
| ***A61K 9/00*** | (2006.01) |
| ***A61K 31/216*** | (2006.01) |
| ***A61K 31/46*** | (2006.01) |
| ***A61P 17/00*** | (2006.01) |

(52) U.S. Cl.
CPC ........ *A61K 31/4015* (2013.01); *A61K 9/0014* (2013.01); *A61K 31/216* (2013.01); *A61K 31/46* (2013.01); *A61P 17/00* (2018.01)

(58) Field of Classification Search
CPC ..... A61K 31/40; A61K 31/4015; A61P 43/00; A61P 17/00; A61Q 15/00
See application file for complete search history.

(56) References Cited

U.S. PATENT DOCUMENTS

| | | | | |
|---|---|---|---|---|
| 6,433,003 | B1 * | 8/2002 | Bobrove | A61K 31/216 514/424 |
| 2003/0064040 | A1 | 4/2003 | Lukacsko | |
| 2010/0082088 | A1 | 4/2010 | Fassih et al. | |
| 2015/0037269 | A1 | 2/2015 | Dumitrescu et al. | |
| 2018/0369097 | A1 | 12/2018 | Zinger | |

FOREIGN PATENT DOCUMENTS

| | | | | |
|---|---|---|---|---|
| EP | 3023538 | A1 | 5/2016 | |
| FR | 2135444 | A1 | 12/1972 | |
| WO | WO-2017015485 | A1 * | 1/2017 | A61K 45/06 |

OTHER PUBLICATIONS

International Search Report and Written Opinion mailed Apr. 12, 2021 for International Application No. PCT/US2020/058978, 21 pages.

Grabell et al., "Current and Emerging Medical Therapies for Primary Hyperhidrosis", Dermatology and Therapy, 2017, vol. 7(1), pp. 25-36.

* cited by examiner

*Primary Examiner* — Kevin E Weddington
(74) *Attorney, Agent, or Firm* — Squire Patton Boggs (US) LLP

(57) ABSTRACT

Disclosed herein are methods for palmar or plantar administration of anticholinergic compounds to a subject in need thereof. Also disclosed herein are methods of treating palmar or plantar hyperhidrosis in a subject in need thereof by administering anticholinergic compounds to the palmar or plantar skin of the subject.

27 Claims, 4 Drawing Sheets

| Test Article | ET-50 | Expected *in vivo* Irritancy |
|---|---|---|
| **Formulation I** | < 24 hours | Moderate to mild |
| **Formulation II** | 24 hours | Very mild to non-irritating |
| **Formulation III** | 24 hours | Very mild to non-irritating |
| **Formulation IV** | >24 hours | Non-irritating |
| **Formulation V** | >24 hours | Non-irritating |
| **Formulation VI** | <hours | Moderate to mild |

METHODS FOR PALMAR OR PLANTAR ADMINISTRATION OF PHARMACEUTICAL COMPOSITIONS

CROSS-REFERENCE TO RELATED APPLICATIONS

The present application is a 35 U.S.C. 371 national-phase filing of International Application No. PCT/US2020/058978, filed on Nov. 4, 2020, which claims the benefit of U.S. 62/931,139, filed on Nov. 5, 2019, the entire contents of both of which are herein incorporated by reference in their entirety for all purposes.

FIELD

The present disclosure sets forth methods for palmar or plantar administration of anticholinergic compounds to a subject in need thereof. Also disclosed herein are methods of treating palmar or plantar hyperhidrosis in a subject in need thereof by administering anticholinergic compounds to the palmar or plantar skin of the subject.

BACKGROUND

Hyperhidrosis is a condition of excessive sweating beyond what is physiologically required to maintain normal thermal regulation. Sweat is produced by glands in the skin and released to the skin surface through ducts. Sweat gland activity is controlled by the nervous system. The nervous system transmits signals to the sweat glands through the neurotransmitter acetylcholine. Primary hyperhidrosis, which is excessive sweating without a known cause, is localized and characteristically symmetric. It can affect the underarms, palms of the hands, soles of the feet, face (including neck and scalp), backs of the knees, trunk, groin, and other areas of the body. Several studies have demonstrated that excessive sweating often impedes normal daily activities and can result in occupational, emotional, psychological, social, and physical impairment.

In the United States, based on the most recent data available, the prevalence of hyperhidrosis is estimated to be between 2.8-4.8%. See Strutton et al., *J. Am. Acad. Dermatol.,* 2005, 51:241-248 and Doolittle et al., *Arch. Dermatol. Res,* 2016, 308(10:743-749. Approximately half of subjects afflicted with hyperhidrosis have axillary (underarm) hyperhidrosis.

A variety of treatments are available for hyperhidrosis, including antiperspirants containing metal salts (e.g., aluminum chloride), injection of botulinum toxin (Botox®), treatment with microwave heating devices, iontophoresis, surgical removal of sweat glands, and systemic or local treatment with anticholinergic compounds. Recently, glycopyrronium tosylate (Qbrexza®) has been approved in the United States for treatment of axillary hyperhidrosis.

However, conventional formulations and conventional modes of administration have significant limitations for treating palmar or plantar hyperhidrosis. Delivery to the thicker palmar and plantar skin is an obstacle to effective treatment of palmar or plantar hyperhidrosis. There is therefore a need for methods for the treatment of palmar or plantar hyperhidrosis that effectively deliver treatment to palmar or plantar skin.

SUMMARY

These and other needs are addressed by the methods provided herein. In one aspect, provided herein are methods for palmar or plantar administration of a compound to a subject in need thereof. The methods comprise the steps of administering the compound to the palmar or plantar skin of the subject; and occluding the palmar or plantar skin of the subject for a time sufficient for the compound to have a therapeutic effect on the palmar or plantar skin of the subject. Useful compounds, compositions, methods of administration, and methods of occluding are described herein.

In certain embodiments, the methods are useful for delivering an effective amount of an anticholinergic compound to the palmar or plantar skin of a subject. In certain embodiments, the methods are useful for treating palmar hyperhidrosis. In certain embodiments, the methods are useful for treating plantar hyperhidrosis.

BRIEF DESCRIPTIONS OF THE DRAWINGS

Figures 2, 3:
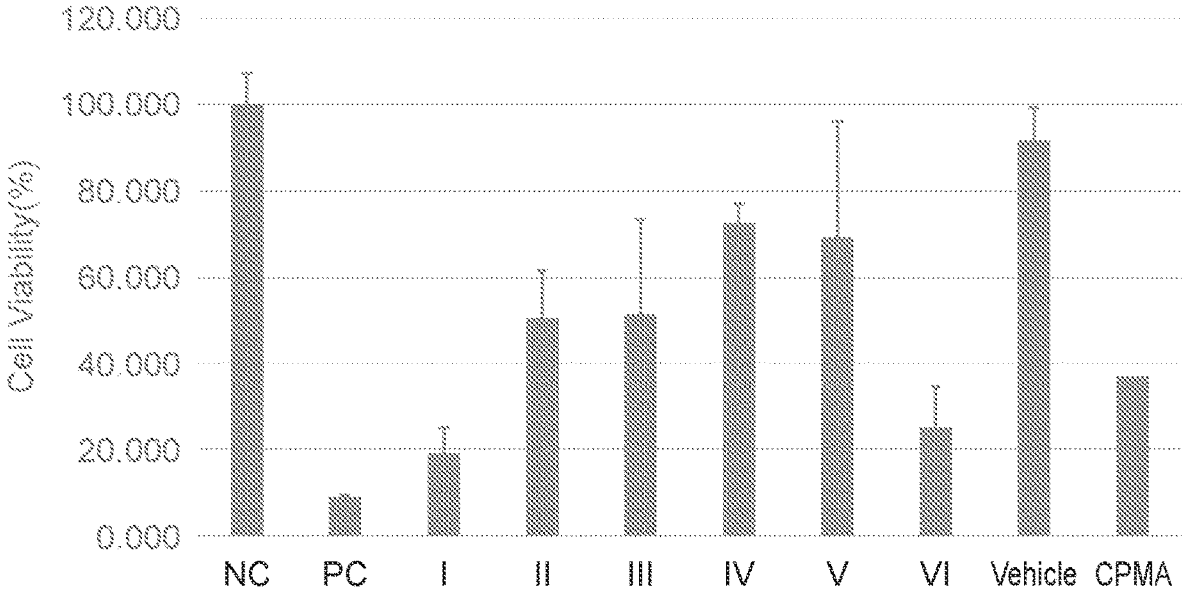
FIG. 2 shows the results of cell viability assays of Formulations I-VI, the vehicle buffer, and the degradant CPMA.

FIG. 3 provides the expected in vivo irritancy levels for Formulations I-VI based on skin irritation assay results.

Figure 4A:
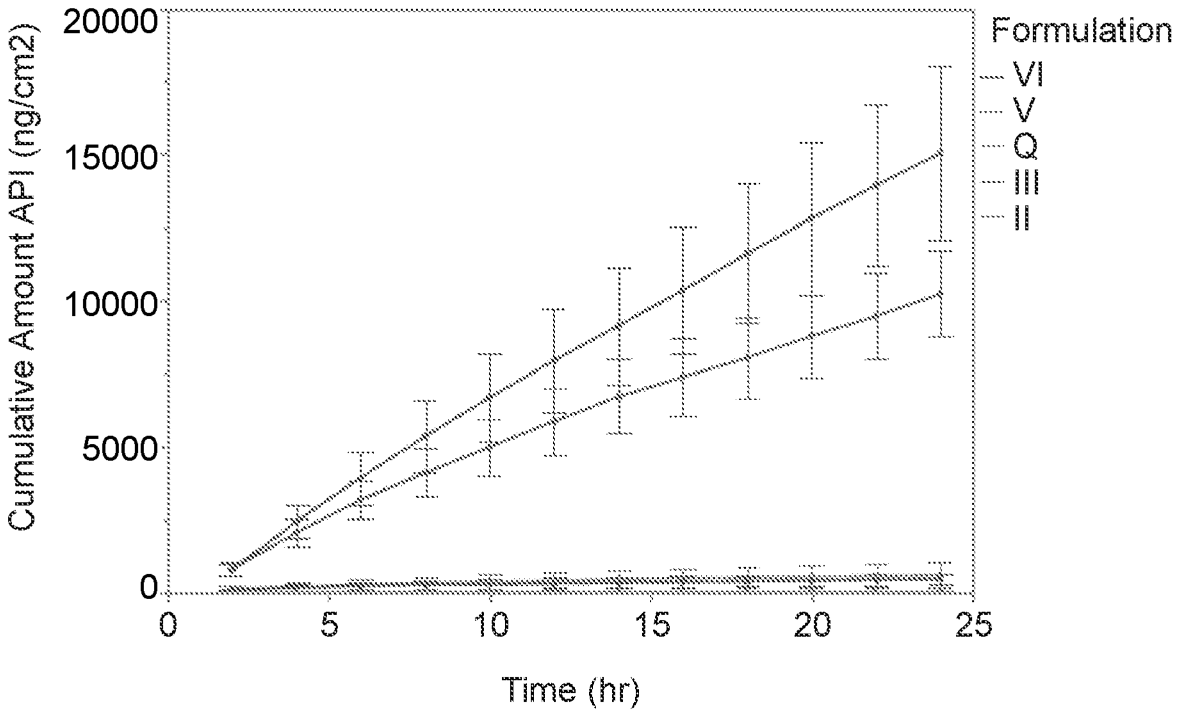
Figure 4B:
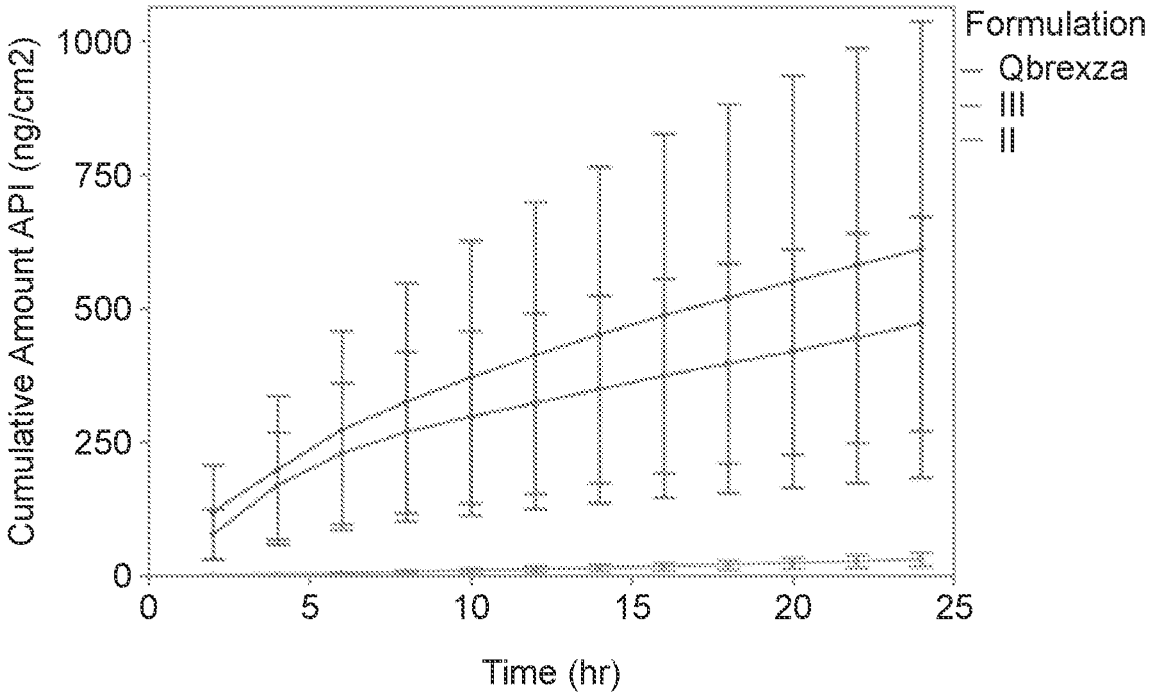

FIG. 4A provides 24 hour data of in vitro full scale permeation studies of Formulations IV, V, I, III and II. FIG. 4B provides expanded results for Formulations I, III, and II.

Figure 5:
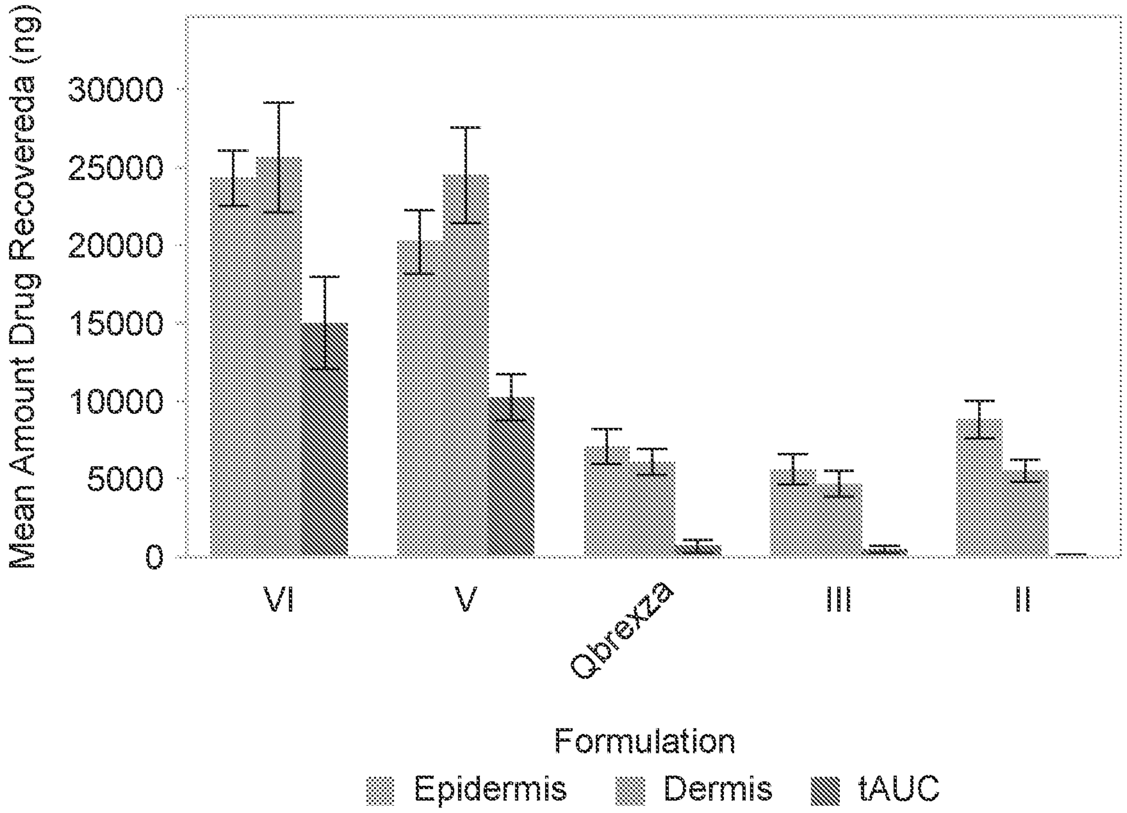

FIG. 5 provides results for recovery (mean amount of drug recovered) of test Formulations VI, V, I, III, and II from epidermal and dermal tissues 24 hours post-application.

DETAILED DESCRIPTION

Set forth herein are methods for palmar and plantar administration and methods for palmar and plantar treatment.

A. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures known in the art that are described or referenced herein are generally well understood and commonly employed using conventional methodologies by those skilled in the art.

As used herein, the singular forms “a,” “an,” and “the” include the plural referents unless the context clearly indicates otherwise.

As used herein, the term “about” refers to the stated value plus or minus 10%, plus or minus 5%, or plus or minus 1%. For example, a value of “about 10” can encompass a range of 9 to 11. For logarithmic scales, the term “about” refers to the stated value plus or minus 0.3 log units, or plus or minus 0.2 log units, or plus or minus 0.1 log units. For example, a value of “about pH 4.6” can encompass a pH range of 4.5-4.7.

As used herein, “treating” or “treatment” of hyperhidrosis refers, in certain embodiments, to ameliorating hyperhidrosis that exists in a subject. In some embodiments, “treating” or “treatment” includes ameliorating at least one physical parameter of hyperhidrosis, such as sweating. In some embodiments, "treating" or "treatment" includes modulating the hyperhidrosis. In some embodiments, "treating" or "treatment" includes delaying or preventing the onset of hyperhidrosis (e.g., a prophylactic treatment). In some embodiments, "treating" or "treatment" includes mitigating the incidence of episodes of hyperhidrosis, by periodic administration of a pharmaceutical composition according to the methods provided herein.

As used herein, the term "therapeutically effective amount" or "effective amount" refers to an amount of a composition provided herein that is useful for treating hyperhidrosis.

As used herein, the term "effective hyperhidrosis treatment" includes any treatment that may be used in treating hyperhidrosis. Any suitable effective hyperhidrosis treatment may be used in the methods provided herein. Illustrative suitable effective hyperhidrosis treatments include, for example, agents for the treatment of hyperhidrosis as described elsewhere in this disclosure (e.g., anticholinergic agents, metal salts, or toxins), microwave heating, iontophoresis, surgical removal of sweat glands, sympathectomy, ultrasound, and laser-based treatment. In particular embodiments, agent is a glycopyrronium compound.

As used herein, the terms "subject" and "patient" mean a mammalian subject. Exemplary subjects include, but are not limited to humans, monkeys, cows, horses, camels, goats and sheep. In certain embodiments, the subject is a human.

As used herein, the term "alkyl" refers to a monovalent and saturated hydrocarbon radical moiety. Alkyl is optionally substituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl.

As used herein, the term "cycloalkyl" refers to a cyclic alkyl. Cycloalkyl is optionally substituted. Examples of cycloalkyl moieties include, but are not limited to, cyclopropyl, cyclobutyl, cyclopentyl, cyclohexyl, cycloheptyl, and cyclooctyl.

As used herein, "alkoxy" refers to a monovalent and saturated hydrocarbon radical moiety wherein the hydrocarbon includes a single bond to an oxygen atom and wherein the radical is localized on the oxygen atom e.g. $CH_3CH_2$—$O^-$ for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, the term "alkoxycarbonyl," refers to a monovalent and saturated hydrocarbon radical moiety wherein the hydrocarbon includes a single carbon bond to an oxygen atom, which is further bonded to a carbonyl, e.g., C(O). The oxygen atom is a bivalent atomic linker between the alkyl portion of the alkoxycarbonyl and the carbonyl. The radical in alkoxycarbonyl is localized on the carbon atom of the carbonyl which is bonded to an oxygen atom of an alkoxy e.g. $CH_3CH_2$—O—C(O). Alkoxycarbonyl substituents bond to the compound which they substitute through this carbonyl carbon atom. Alkoxycarbonyl is optionally substituted and can be linear or branched. Alkoxycarbonyl includes, but is not limited to, those having 1-20 carbon atoms, i.e., $C_{1-20}$ alkoxycarbonyl; 1-12 carbon atoms, i.e., $C_{1-12}$ alkoxycarbonyl; 1-8 carbon atoms, i.e., $C_{1-8}$ alkoxycarbonyl; 1-6 carbon atoms, i.e., $C_{1-6}$ alkoxycarbonyl; and 1-3 carbon atoms, i.e., $C_{1-3}$ alkoxycarbonyl. Examples of alkoxy moieties include, but are not limited to methoxycarbonyl, and ethoxycarbonyl.

As used herein, the phrase "stereomerically pure," refers to a particular stereoisomer of a compound which is present to a greater extent than other stereoisomers of that compound, e.g., the compound is present in diastereomeric excess or the compound is present in enantiomeric excess. In some embodiments, the stereomerically pure compounds described herein include 80% or greater, 85% or greater, 90% or greater, 95% or greater, or 97% or greater by weight of one stereoisomer of the compound. In some embodiments, the stereomerically pure compounds described herein include 80% or greater, 85% or greater, 90% or greater, 95% or greater, or 97% or greater by mole of one stereoisomer of the compound.

In the above definitions, "optionally substituted" indicates optional substitution with halogen, hydroxyl, methoxy, amino, or cycloalkyl. Unless specified otherwise, substituents are not further substituted.

As used herein, the phrase "pharmaceutically acceptable counter ion" refers to ions which retain the biological effectiveness and properties of the glycopyrronium base, which are not biologically or otherwise undesirable, and which carry an anionic charge. The glycopyrronium base forms salts by virtue of the presence of the quaternary ammonium thereon. The pharmaceutically acceptable counter ion may be prepared from inorganic or organic acids. Salts derived from inorganic acids include, but are not limited to, hydrochloric acid, hydrobromic acid, hydrogen fluoride, hydrogen iodide, sulfuric acid, nitric acid, phosphoric acid, and the like. Salts derived from organic acids include, but are not limited to, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. In some embodiments, the salt is derived from p-toluene sulfonic acid or hydrobromic acid.

B. Methods of Administration and Treatment

The present disclosure provides methods for administering therapeutic compounds to palmar or plantar skin. In certain embodiments, the skin is palmar. In certain embodiments, the skin is plantar. In certain embodiments, the administration is to palmar skin and to plantar skin. In certain embodiments, the therapeutic compounds target site of activity is the epidermal or dermal layer of the skin, or in tissue with or adjacent to sweat glands.

The administration can be for any purpose deemed suitable by the practitioner of skill. In certain embodiments, the methods are for therapy. In certain embodiments, the methods are for prophylaxis. In certain embodiments, the methods are for therapy and for prophylaxis.

In particular embodiments, the methods are for treating or preventing a disease or disorder in a subject in need thereof. In certain embodiments, the methods are for treating or preventing hyperhidrosis in a subject in need thereof. In certain embodiments, the methods are for treating palmar hyperhidrosis in a subject in need thereof. In certain embodiments, the methods are for treating plantar hyperhidrosis in a subject in need thereof. In certain embodiments, the methods are for preventing palmar hyperhidrosis in a subject in need thereof. In certain embodiments, the methods are for preventing plantar hyperhidrosis in a subject in need thereof.

The subject can be any subject deemed suitable by the practitioner of skill. In certain embodiments, the subject is a mammal. In certain embodiments, the subject is a human. In certain embodiments, the subject is an adult human. In certain embodiments, the subject is a pediatric human.

In the methods, the compound is any compound deemed suitable for palmar or plantar administration by the practitioner of skill. In certain embodiments, the compound is an anticholinergic compound. The practitioners of skill will recognize that such methods are useful for treating any cholinergic disease or disorder where palmar or plantar administration is useful. In certain embodiments, the anticholinergic compound is selected from the group consisting of a glycopyrronium compound, a sofpironium compound, propantheline, oxybutynin, methantheline, and benztropine. In particular embodiments, the compound is glycopyrronium bromide. In particular embodiments, the compound is glycopyrronium tosylate monohydrate. In particular embodiments, the compound is sofpironium bromide. In each embodiment, the compound can be administered itself, or as a pharmaceutically acceptable salt or solvate. In certain embodiments, the compound is administered in a pharmaceutical composition further comprising one or more pharmaceutically acceptable carriers, excipients, or diluents. Particular useful compounds are described in the sections below.

In the methods, the compound is administered to the palmar or plantar skin of the subject. The administration can be by any technique deemed suitable by the practitioner of skill. In certain embodiments, the administration is by direct application of a pharmaceutical composition to the skin of the subject. In certain embodiments, the administration is with a wipe, swab, applicator, roll-on, stick, spray, or dropper.

The administration can be in any dose deemed suitable by the practitioner of skill. In certain embodiments, the compound is an anticholinergic compound, and the dose is from about 0.1 mg to about 500 mg. In certain embodiments, the compound is an anticholinergic compound, and the dose is from about 0.1 mg to about 400 mg. In certain embodiments, the compound is an anticholinergic compound, and the dose is from about 0.1 mg to about 300 mg. In certain embodiments, the compound is an anticholinergic compound, and the dose is from about 0.1 mg to about 200 mg. In certain embodiments, the compound is an anticholinergic compound, and the dose is from about 0.1 mg to about 100 mg. In certain embodiments, the compound is an anticholinergic compound, and the dose is from about 0.1 mg to about 75 mg. In certain embodiments, the compound is an anticholinergic compound, and the dose is from about 0.1 mg to about 50 mg. In certain embodiments, the compound is an anticholinergic compound, and the dose is from about 0.1 mg to about 30 mg. In certain embodiments, the compound is an anticholinergic compound, and the dose is from about 0.1 mg to about 25 mg. In certain embodiments, the compound is an anticholinergic compound, and the dose is from about 0.1 mg to about 20 mg. In certain embodiments, the compound is an anticholinergic compound, and the dose is from about 0.1 mg to about 10 mg. In certain embodiments, the compound is an anticholinergic compound, and the dose is from about 0.1 mg to about 5 mg. In certain embodiments, the compound is an anticholinergic compound, and the dose is from about 0.1 mg to about 4 mg. In certain embodiments, the compound is an anticholinergic compound, and the dose is from about 0.1 mg to about 3 mg. In certain embodiments, the compound is an anticholinergic compound, and the dose is from about 0.1 mg to about 2 mg.

In certain embodiments, the compound is glycopyrronium, and the dose is from about 0.1 mg to about 66 mg. In certain embodiments, the compound is glycopyrronium, and the dose is from about 0.1 mg to about 50 mg. In certain embodiments, the compound is glycopyrronium, and the dose is from about 0.1 mg to about 25 mg. In certain embodiments, the compound is glycopyrronium, and the dose is from about 0.1 mg to about 20 mg. In certain embodiments, the compound is glycopyrronium, and the dose is from about 0.1 mg to about 15 mg. In certain embodiments, the compound is glycopyrronium, and the dose is from about 0.1 mg to about 10 mg. In certain embodiments, the compound is glycopyrronium, and the dose is from about 0.1 mg to about 5 mg. In certain embodiments, the compound is glycopyrronium, and the dose is from about 0.1 mg to about 2.5 mg. In certain embodiments, the compound is glycopyrronium, and the dose is from about 0.1 mg to about 2 mg.

In certain embodiments, the compound is glycopyrronium tosylate monohydrate, and the dose is from about 0.1 mg to about 105 mg. In certain embodiments, the compound is glycopyrronium tosylate monohydrate, and the dose is from about 0.1 mg to about 100 mg. In certain embodiments, the compound is glycopyrronium tosylate monohydrate, and the dose is from about 0.1 mg to about 75 mg. In certain embodiments, the compound is glycopyrronium tosylate monohydrate, and the dose is from about 0.1 mg to about 50 mg. In certain embodiments, the compound is glycopyrronium tosylate monohydrate, and the dose is from about 0.1 mg to about 25 mg. In certain embodiments, the compound is glycopyrronium tosylate monohydrate, and the dose is from about 0.1 mg to about 20 mg. In certain embodiments, the compound is glycopyrronium tosylate monohydrate, and the dose is from about 0.1 mg to about 15 mg. In certain embodiments, the compound is glycopyrronium tosylate monohydrate, and the dose is from about 0.1 mg to about 10 mg. In certain embodiments, the compound is glycopyrronium tosylate monohydrate, and the dose is from about 0.1 mg to about 5 mg. In certain embodiments, the compound is glycopyrronium tosylate monohydrate, and the dose is from about 0.1 mg to about 3 mg.

In certain embodiments, the administration is via a single application (i.e., a single swipe). In certain embodiments, the administration is via two applications. In certain embodiments, the administration is via three applications. In certain embodiments, the administration is via four applications. In certain embodiments, the administration is via three applications. In certain embodiments, the administration is via five applications. In certain embodiments, the administration is via six applications. In certain embodiments, the administration is via seven applications. In certain embodiments, the administration is via eight applications. In certain embodiments, the administration is via nine applications. In certain embodiments, the administration is via ten applications. In certain embodiments, the administration is via more than ten applications. In some embodiments, each wipe is applied to palmar or plantar surfaces continuously until wipe is dry. In some embodiments, administration comprises the use of one or more wipes to provide one or more applications. In certain embodiments, the wipe is squeezed to apply all or almost all of the solution in the wipe, i.e. up to 2 g solution or even up to 2.8 g solution.

The administration can be for any length of time deemed suitable by the practitioner of skill. In certain embodiments, the compound is administered for 1-10 minutes, 1-3 minutes, 1-5 minutes, or for about 1 minute. In certain embodiments, the administration is via a wipe, roll-on, stick, or other applicator.

Following administration of the compound, the skin of the subject is occluded. Occlusion is helpful to facilitate delivery and helpful to prevent transfer to others, for instance to other humans or to pets. In certain embodiments, the skin of the subject is occluded with a material. The material can be any material deemed suitable for occlusion by the practitioner of skill. In certain embodiments, the material is fully occlusive. In certain embodiments, the material is partially occlusive or semi-occlusive. In certain embodiments, the material is cotton. In certain embodiments, the material is 95-100% cotton. In certain embodiments, the material is about 100% cotton. In certain embodiments, the material is nitrile. In certain embodiments, the material is polyethylene, for instance Saran Wrap. In certain embodiments, the material is latex. In certain embodiments, the material is plastic. In certain embodiments, the material is butyl rubber. In certain embodiments, the material is neoprene. In certain embodiments, the material is polyester. In certain embodiments, the material is wool. In certain embodiments, the material is rayon. In certain embodiments, the material is acrylic fiber.

The material can be in any form deemed suitable by the practitioner of skill. In certain embodiments, the material is a wrap applied to the skin of the subject. In certain embodiments, the administration is palmar, and the material is in the form of a glove or mitten. In certain embodiments, the administration is plantar, and the material is in the form of a sock.

The occluding can be for any length of time deemed suitable by the practitioner of skill. In certain embodiments, the occluding is for 0.5-12 hours, 1-10 hours, 1-8 hours, or 1-5 hours. In certain embodiments, the occluding is for about 8 hours. In certain embodiments, the occluding is overnight.

The administration can be repeated as deemed needed by the practitioner of skill. In certain embodiments, the administration is once per day. In certain embodiments, the administration is twice per day. In certain embodiments, the administration is three times per day. In certain embodiments, the administration is four times per day. In certain embodiments, the administration is 2-3 times per day for a few days followed by once per day for a few days. The number of days can be determined by the practitioner of skill. In certain embodiments, the administration is 2-3 times per day for 2-3 days followed by once per day for 4-5 days.

The administration can continue for any length of time deemed suitable by the practitioner of skill. In certain embodiments, the administration is for one day. In certain embodiments, the administration is for one week. In certain embodiments, the administration is for two weeks. In certain embodiments, the administration is for three weeks. In certain embodiments, the administration is for four weeks. In certain embodiments, the administration continues as needed while symptoms are evident. The administration can be at any interval deemed suitable by the practitioner of skill. In certain embodiments, the administration is every day. In certain embodiments, the administration is every other day. In certain embodiments, the administration is four days per week. In certain embodiments, the administration is three days per week. In certain embodiments, the administration is two days per week. In certain embodiments, the administration is one day per week.

The administration can be monitored by any technique deemed suitable by the practitioner of skill. For hyperhidrosis, the administration can be followed by one or more questionnaires known to the practitioner of skill. In certain embodiments, treatment of hyperhidrosis can be monitored by the Hyperhidrosis Disease Severity Scale (HDSS). See Solish et al., *Dermatol. Surg.*, 2007, 33:908-923, incorporated by reference in its entirety. In certain embodiments, the Axillary Sweating Daily Diary (ASDD) can be adapted for palmar assessment. See Nelson et al., 2019, *J. Patient Rep Outcomes* 3(1):59, incorporated by reference in its entirety. In certain embodiments, the Axillary Sweating Daily Diary (ASDD) can be adapted for plantar assessment.

C. Compounds and Pharmaceutical Compositions

In the methods described herein, the compound can be any compound deemed suitable for palmar or plantar administration by the practitioner of skill. In certain embodiments, the compound is an anticholinergic compound. In certain embodiments, the compound is effective for the treatment of hyperhidrosis.

In certain embodiments, the anticholinergic agent is selected from a glycopyrronium compound, propantheline, oxybutynin, methantheline, benztropine, and sofpironium bromide (BBI-4000; Brickell Biotech, Inc.). In some embodiments, the agent is a glycopyrronium compound. In some embodiments, the glycopyrronium compound is glycopyrronium tosylate monohydrate. In some embodiments, the glycopyrronium compound is glycopyrronium bromide. In certain embodiments, the compound is sofpironium bromide.

In some embodiments, the glycopyrronium compound is threo-glycopyrronium tosylate monohydrate. In some embodiments, the glycopyrronium compound is threo-glycopyrronium bromide.

In some embodiments, the glycopyrronium compound comprises threo-glycopyrronium and erythro-glycopyrronium, wherein the threo-glycopyrronium is at least 95% of the total glycopyrronium content of the composition and the erythro-glycopyrronium is less than 5%, less than 4%, less than 3%, less than 2%, less than 1%, less than 0.8%, less than 0.7%, less than 0.6%, less than 0.5%, or less than 0.4% of the total glycopyrronium content of the composition. In some embodiments, the glycopyrronium compound comprises threo-glycopyrronium and erythro-glycopyrronium, wherein the threo-glycopyrronium is at least 95% of the total glycopyrronium content of the composition, and the erythro-glycopyrronium is less than 0.4% of the total glycopyrronium content of the composition.

In certain embodiments, the methods comprise administration of a compound of Formula (I):

(I)

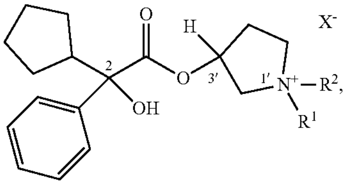

In Formula (I), $R^1$ and $R^2$ are each, independently in each instance, selected from alkyl and alkyl substituted with alkoxycarbonyl; and $X^-$ is an anion. In certain embodiments, $X^-$ is bromide. In certain embodiments, $X^-$ is tosylate. In certain embodiments, alkyl is not further substituted, and alkoxycarbonyl is not substituted.

In certain embodiments, the methods comprise administration of a compound of Formula (I) wherein $R^1$ and $R^2$ are each, independently in each instance, selected from alkyl and alkyl substituted with alkoxycarbonyl; the stereochemical configuration about the carbon atoms indicated by 2 and 3 is a threo mixture, i.e. R/S and S/R; and $X^-$ is an anion. In certain embodiments, $X^-$ is bromide. In certain embodiments, $X^-$ is tosylate. In certain embodiments, alkyl is not further substituted, and alkoxycarbonyl is not substituted.

In certain embodiments, the methods comprise administration of a compound of Formula (I) wherein $R^1$ and $R^2$ are each, independently in each instance, selected from alkyl and alkyl substituted with alkoxycarbonyl; the stereochemical configuration about the carbon atom indicated by 2 is R; the stereochemical configuration about carbon atom indicated by 3' is R; and $X^-$ is an anion. In certain embodiments, $X^-$ is bromide. In certain embodiments, $X^-$ is tosylate. In certain embodiments, alkyl is not further substituted, and alkoxycarbonyl is not substituted.

In certain embodiments, $R^1$ is alkyl. In certain embodiments, $R^1$ is methyl, ethyl, n-propyl, i-propyl, n-butyl, t-butyl, i-butyl, n-pentyl, or i-pentyl. In some examples, $R^1$ is methyl or ethyl. In certain embodiments, $R^1$ is methyl. In other examples, $R^1$ is ethyl.

In certain embodiments, $R^2$ is alkyl. In certain embodiments, $R^2$ is methyl, ethyl, n-propyl, i-propyl, n-butyl, t-butyl, i-butyl, n-pentyl, or i-pentyl. In certain embodiments, $R^2$ is methyl or ethyl. In certain embodiments, $R^2$ is methyl. In certain embodiments, $R^2$ is ethyl. In some examples, both $R^1$ and $R^2$ are methyl.

In certain embodiments, $R^1$ is alkyl substituted with alkoxycarbonyl. In certain embodiments, $R^1$ is methyl substituted with alkoxycarbonyl. In certain embodiments, $R^1$ is $—CH_2C(O)OCH_2CH_3$. In certain embodiments, $R^2$ is alkyl. In certain embodiments, $R^2$ is methyl or ethyl. In certain embodiments, $R^2$ is methyl. In certain embodiments, $R^2$ is ethyl.

In some examples, the compound of Formula (I) is

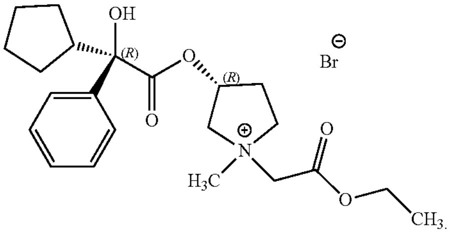

In some examples, the compound is [(3R)-1-(2-ethoxy-2-oxoethyl)-1-methylpyrrolidin-1-ium-3-yl](2R)-2-cyclopentyl-2-hydroxy-2-phenylacetate; bromide.

In some examples, the compound of Formula (I) is

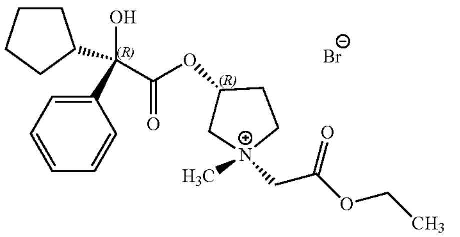

or

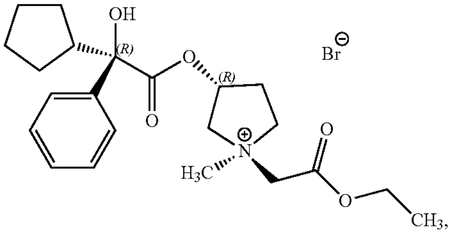

or a mixture thereof.

In some examples, the compound of Formula (I) is a threo mixture of:

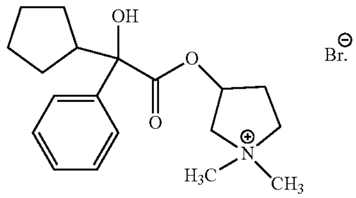 [SMILES: C[N+]1(C)CCC(OC(=O)C(O)(c2ccccc2)C2CCCC2)C1 ; "Br."]

In some examples, the compound of Formula (I) is a threo mixture of:

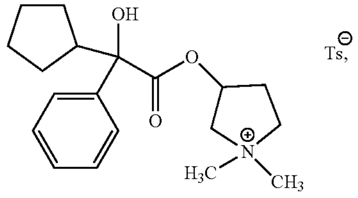 [SMILES: C[N+]1(C)CCC(OC(=O)C(O)(c2ccccc2)C2CCCC2)C1 ; "Ts,"]

wherein $Ts^{(-)}$ indicates a tosylate ion.

In some examples, the compound is a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate. In certain embodiments, some examples, the compound is a racemic mixture of (R)-3-((S)-2-cyclopentyl-2-hydroxy-2-phenylacetoxy)-1,1-dimethylpyrrolidinium bromide and (S)-3-((R)-2-cyclopentyl-2-hydroxy-2-phenylacetoxy)-1,1-dimethylpyrrolidinium bromide.

In some embodiments, including any of the foregoing, the anticholinergic compound has a structure according to Formula (II):

Formula (II)

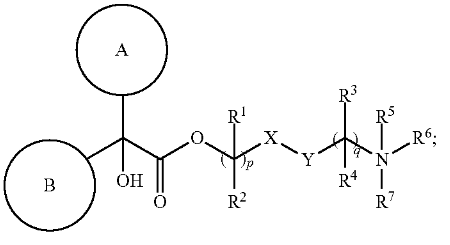

or a pharmaceutically acceptable salt thereof. Compounds of Formula (II) can be made, formulated, and administered according to U.S. Provisional Application No. 62/942,677 filed Dec. 2, 2019, the contents of which are hereby incorporated by reference in their entirety.

In Formula (II), ring A is selected from cycloalkyl, aryl, heterocycloalkyl, or heteroaryl. In some embodiments, ring A is optionally bridged to ring B. In Formula (II), ring B is selected from cycloalkyl, aryl, heterocycloalkyl, or heteroaryl. In some embodiments, ring B is optionally bridged to ring A. In Formula (II), ring A and ring B are each, independently in each instance, optionally substituted with 1-5 substituents selected from $C_{1-3}$ alkyl, $C_{1-3}$alkoxyl, carbonyl, cyano, halo, hydroxyl, —$NO_2$, —$NO_3$, —$SO_2$, —$SO_3$, or —$PO_4$. In certain embodiments, X is O and Y is C═O. In certain other embodiments, X is C═O and Y is O. $R^1$ and $R^2$ are each, independently in each instance, selected from H, $C_{1-3}$alkyl, $C_{1-3}$alkoxyl, carbonyl, cyano, halo, hydroxyl, —$NO_2$, —$NO_3$, —$SO_2$, —$SO_3$, or —$PO_4$. If $R^1$ is carbonyl, then $R^2$ is not carbonyl. If $R^2$ is carbonyl, then $R^1$ is not carbonyl. If $R^3$ is carbonyl, then $R^4$ is not carbonyl. If $R^4$ is carbonyl, then $R^3$ is not carbonyl; $R^3$ and $R^4$ are each, independently in each instance, selected from H, $C_{1-3}$alkyl, $C_{1-3}$alkoxyl, carbonyl, cyano, halo, hydroxyl, —$NO_2$, —$NO_3$, —$SO_2$, —$SO_3$, or —$PO_4$. $R^5$ is $C_{1-3}$alkyl or absent. $R^6$ is $C_{1-3}$alkyl or bonded with $R^7$ to form a five-membered heterocycloalkyl ring. and $R^7$ is H, $C_{1-3}$alkyl, or bonded with $R^6$ to form a five-membered heterocycloalkyl ring. In Formula (I), $R^1$, $R^2$, $R^3$, $R^4$, $R^5$, $R^6$, and $R^7$ are unsubstituted. Subscript p is 1 or 2. Subscript q is 1, 2, or 3. When R5 is absent, the compound is preferably in the form of a pharmaceutically acceptable salt with a pharmaceutically acceptable counterion.

In some embodiments, including any of the foregoing, the compounds having the structure of Formula (II), are selected from Formula (IIa) or Formula (IIb):

Formula (IIa)

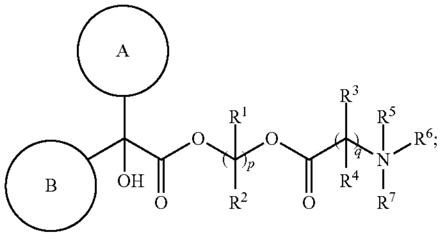

or

-continued

Formula (IIb)

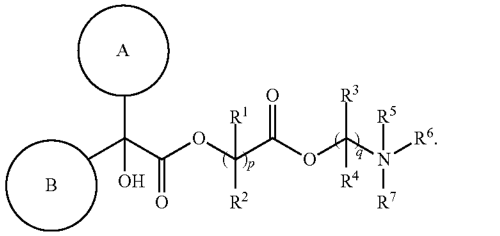

In some embodiments, including any of the foregoing, Ring A and Ring B are each, independently in each instance, either a five- or six-membered cycloalkyl, aryl, heterocycloalkyl, and heteroaryl. In certain embodiments, Ring A is five-membered cycloalkyl, aryl, heterocycloalkyl, and heteroaryl. In certain other embodiments, Ring A is six-membered cycloalkyl, aryl, heterocycloalkyl, and heteroaryl. In certain embodiments, Ring B is five-membered cycloalkyl, aryl, heterocycloalkyl, and heteroaryl. In certain other embodiments, Ring B is six-membered cycloalkyl, aryl, heterocycloalkyl, and heteroaryl. In some embodiments, Ring A is a five-membered cycloalkyl. In some other embodiments, Ring A is a five-membered aryl. In yet other embodiments, Ring A is a five-membered heterocycloalkyl. In still other embodiments, Ring A is a five-membered heteroaryl. In some embodiments, Ring A is a six-membered cycloalkyl. In some other embodiments, Ring A is a six-membered aryl. In yet other embodiments, Ring A is a six-membered heterocycloalkyl. In still other embodiments, Ring A is a six-membered heteroaryl. In some embodiments, Ring B is a five-membered cycloalkyl. In some other embodiments, Ring B is a five-membered aryl. In yet other embodiments, Ring B is a five-membered heterocycloalkyl. In still other embodiments, Ring B is a five-membered heteroaryl. In some embodiments, Ring B is a six-membered cycloalkyl. In some other embodiments, Ring B is a six-membered aryl. In yet other embodiments, Ring B is a six-membered heterocycloalkyl. In still other embodiments, Ring B is a six-membered heteroaryl.

In some embodiments, including any of the foregoing, the compounds having the structure of Formula (II), are selected from Formula (IIc) or Formula (IId):

Formula (IIc)

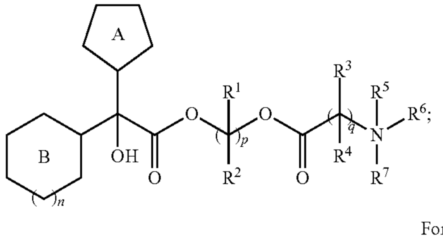

or

Formula (IId)

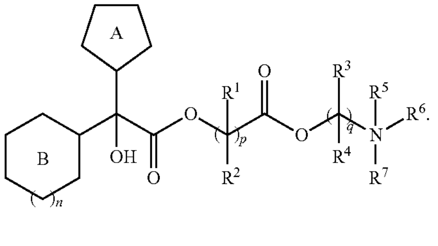

In Formula (IIc) or Formula (IId), subscript n is 0 or 1 such that when n is 0, ring B is a five member ring.

In some embodiments, including any of the foregoing, Ring A and Ring B are unsubstituted. In some embodiments, including any of the foregoing, Ring A is unsubstituted and Ring B is substituted. In some embodiments, including any of the foregoing, Ring A is substituted and Ring B is unsubstituted.

In some embodiments, including any of the foregoing, Ring A and Ring B are not bridged.

In some embodiments, including any of the foregoing, subscript p is 1 or 2. In some embodiments, subscript p is 1. In some other embodiments, subscript p is 2.

In some embodiments, including any of the foregoing, subscript q is 1 or 2. In some embodiments, subscript q is 1. In some other embodiments, subscript q is 2.

In some embodiments, including any of the foregoing, the compounds having the structure of Formula (II), are selected from Formula (IIe) or Formula (IIf):

Formula (IIe)

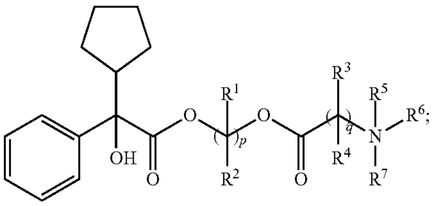

or

Formula (IIf)

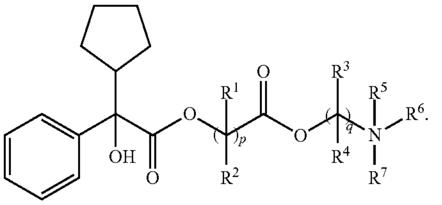

In some embodiments, including any of the foregoing, the compounds having the structure of Formula (II), are selected from Formula (IIg) or Formula (IIh):

Formula (IIg)

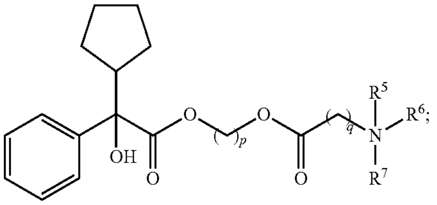

or

Formula (IIh)

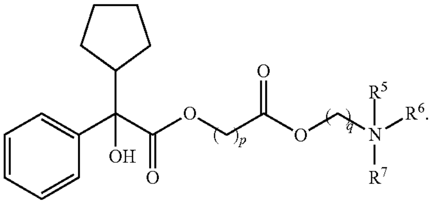

In some embodiments, including any of the foregoing, the compounds having the structure of Formula (II), are selected from Formula (IIi), Formula (IIj), Formula (IIk), Formula (IIl), Formula (IIm) or Formula (IIn):

Formula (IIi)

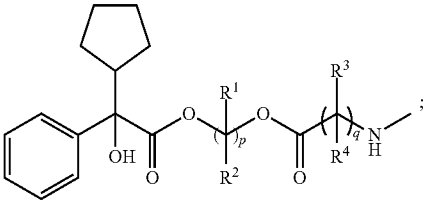

Formula (IIj)

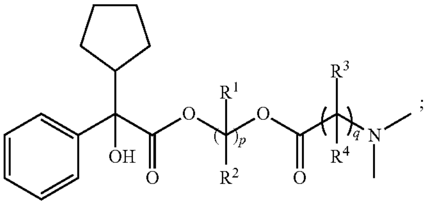

Formula (IIk)

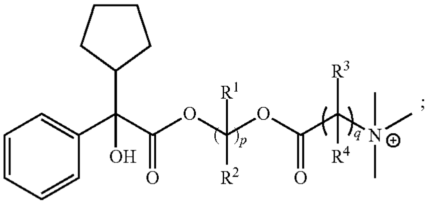

Formula (Il)

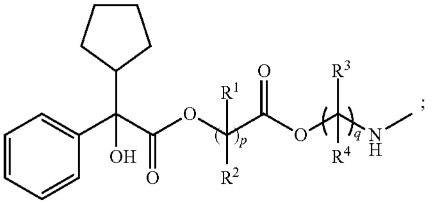

Formula (IIm)

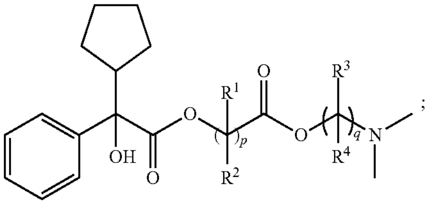

or

Formula (IIn)

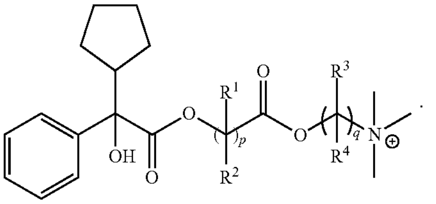

In some embodiments, including any of the foregoing, the compounds having the structure of Formula (II) are selected from Formula (IIo), Formula (IIp), Formula (IIq), Formula (IIr), Formula (IIs), Formula (IIt), Formula (IIu), or Formula (IIv):

Formula (IIo)

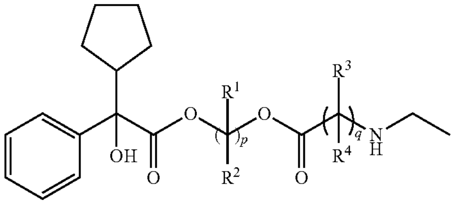

;

Formula (IIp)

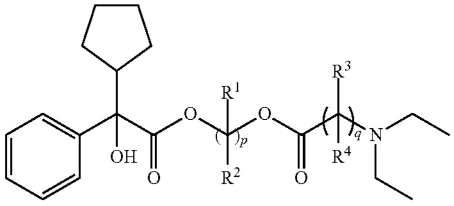

;

Formula (IIq)

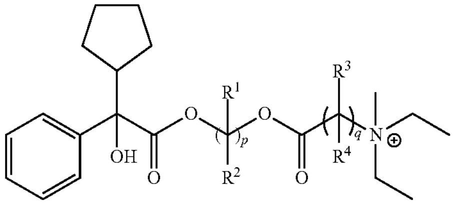

;

Formula (IIr)

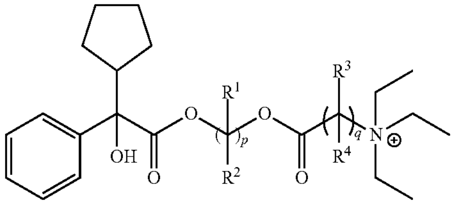

;

Formula (IIs)

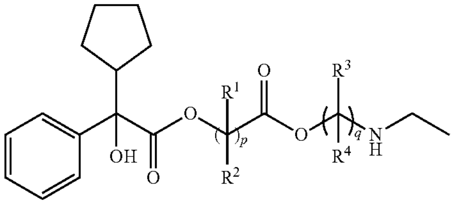

;

Formula (IIt)

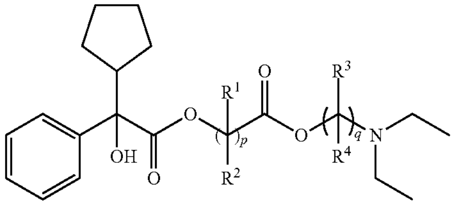

;

Formula (IIu)

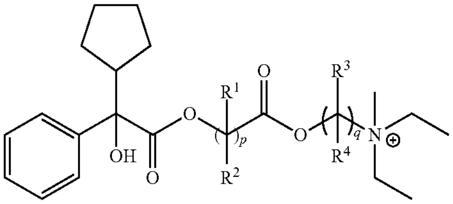

; or

-continued

Formula (IIv)

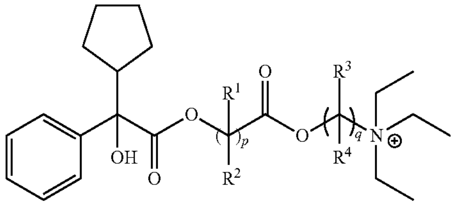

.

In some embodiments, including any of the foregoing, the compounds having the structure of Formula (II) are selected from Formula (IIw), Formula (IIx), Formula (IIy), or Formula (IIz):

Formula (IIw)

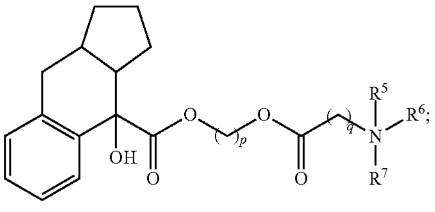

Formula (IIx)

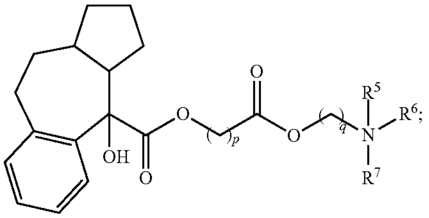

Formula (IIy)

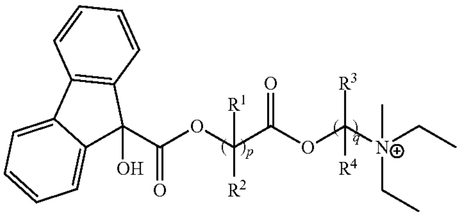

; or

Formula (IIz)

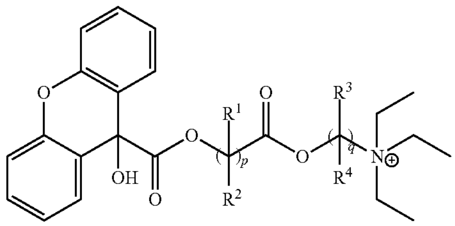

.

In some embodiments, including any of the foregoing, the compounds having the structure of Formula (II) are selected from:

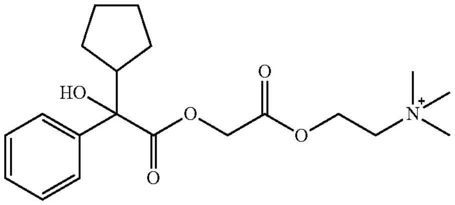
;

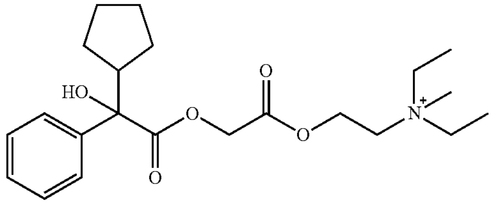
;

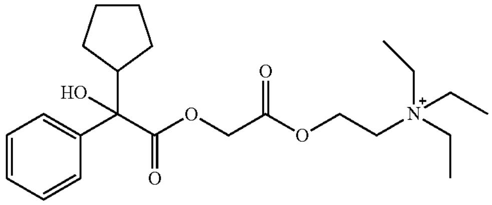
;

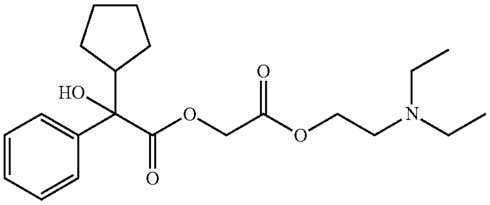
; or

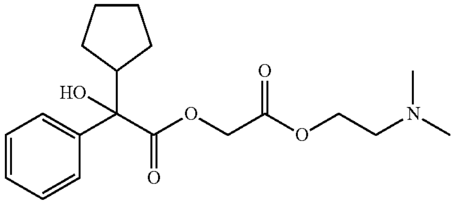
.

In some embodiments, including any of the foregoing, the compounds having the structure of Formula (II) are selected from:

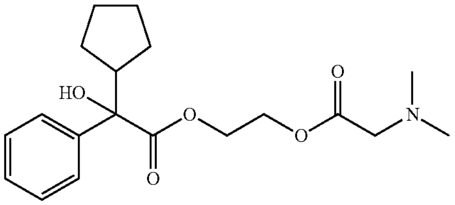
; or

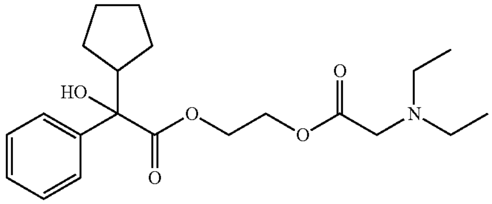
.

In certain embodiments, the compound is stereochemically pure, i.e. in a diastereomeric excess. In certain embodiments, the stereomerically pure stereoisomer of the compound is present in an enantiomeric excess of at least 80%. In certain embodiments, the stereomerically pure stereoisomer of the compound is present in an enantiomeric excess of at least 85%. In certain embodiments, the stereomerically pure stereoisomer of the compound is present in an enantiomeric excess of at least 90%. In certain embodiments, the stereomerically pure stereoisomer of a compound of the compound is present in an enantiomeric excess of at least 95%. In certain embodiments, the stereomerically pure stereoisomer of a compound of the compound is present in an enantiomeric excess of at least 99%. In certain embodiments, the stereomerically pure stereoisomer of a compound of the compound is present in an enantiomeric excess of at least 99.6%. In certain embodiments, the stereomerically pure stereoisomer of the compound is present in a diastereomeric excess of at least 80%. In certain embodiments, the stereomerically pure stereoisomer of the compound is present in a diastereomeric excess of at least 85%. In certain embodiments, the stereomerically pure stereoisomer of the compound is present in a diastereomeric excess of at least 90%. In certain embodiments, the stereomerically pure stereoisomer of the compound is present in a diastereomeric excess of at least 95%. In certain embodiments, the stereomerically pure stereoisomer of the compound is present in a diastereomeric excess of at least 99%.

In some examples, the compounds are formulated with a pharmaceutically acceptable excipient, diluent, or salt.

In some examples, set forth herein is a pharmaceutical composition, include a compound prepared by a method set forth herein. In some examples, the composition is formulated as a topical.

In some embodiments, the methods provided herein may further comprise administration of one or more additional agents, for instance to treat hyperhidrosis. Illustrative additional agents include any of those described in this disclosure or known in the art for the treatment of hyperhidrosis. The additional agent(s) may be administered in the same pharmaceutical composition as the agent recited in the methods provided herein, or in a different pharmaceutical composition, according to the judgment of those of skill in the art.

In some embodiments, the methods provided herein comprises administering a compound in combination with another agent or procedure. In some aspects, the other agent or procedure is selected from an anticholinergic agent, a metal salt, and a toxin.

In some embodiments, topical administration of an agent is combined with systemic administration of the same agent, or a different agent. In some aspects, topical administration of a glycopyrronium compound is combined with systemic administration of the glycopyrronium compound.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

The present disclosure includes pharmaceutical compositions of the compounds described herein, e.g., compositions comprising a compound described herein, a salt, stereoisomer, mixture of stereoisomers, polymorph thereof, and a pharmaceutically acceptable carrier, diluent, and/or excipient. Examples of suitable carriers, diluents and excipients include, but are not limited to: buffers for maintenance of proper composition pH (e.g., citrate buffers, succinate buffers, acetate buffers, phosphate buffers, lactate buffers, oxalate buffers and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants. In some embodiments, pharmaceutical compositions to be delivered via solid carriers, e.g., sticks, can be formulated with one or more of the following group consisting of hydrophilic carriers, water, gelling agents, clarifying agents, solubilizers, antimicrobial agents, chelating agents, neutralizing agents, and antioxidants.

The compounds or compositions described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference in its entirety for all purposes.

A pharmaceutical composition can comprise a unit dose formulation, where the unit dose is a dose sufficient to have a therapeutic or suppressive effect or an amount effective to modulate or treat a disease or condition described herein. The unit dose may be sufficient as a single dose to have a therapeutic or suppressive effect or an amount effective to modulate or treat a disease or condition described herein. Alternatively, the unit dose may be a dose administered periodically in a course of treatment or suppression of a disorder, or to modulate or treat a disease or condition described herein.

Pharmaceutical compositions containing the compounds or compositions of the invention may be in any form suitable for the intended method of administration, including, for example, a solution, a suspension, or an emulsion. In some examples, the compositions set forth herein are suitable for topical application. In some examples, liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. In some embodiments, the pharmaceutical composition is delivered using solid carriers, such as gels or solid sticks.

The compounds or compositions of the invention may be administered topically in dosage unit formulations containing conventional nontoxic pharmaceutically acceptable carriers, adjuvants, and vehicles as desired. Topical administration may also involve the use of transdermal administration such as transdermal patches or iontophoresis devices. The compounds or compositions are mixed with pharmaceutically acceptable carriers, adjuvants, and vehicles appropriate for the desired route of administration. The compounds described for use herein can be administered in solid form, in liquid form, in aerosol form, or in the form of creams, solutions, other emulsions, dispersions, balms, gels, including, but not limited to gel sticks, solid sticks, and in other suitable forms. The compounds can also be administered as prodrugs, where the prodrug undergoes transformation in the treated subject to a form which is therapeutically effective. Additional methods of administration are known in the art.

Compositions of the invention may be formulated to act at the epidermal layer, the dermal layer, or more deeply, i.e., greater than 500 M deep, in tissue at, adjacent, or near sweat glands.

In certain embodiments, the pharmaceutical composition is a topical dosage form comprising about 2.8 g of alcohol: water solution comprising the glycopyrronium compound with a pH buffering agent. In an embodiment, the glycopyrronium compound is present at a concentration of about 0.25-20% (w/w). In some embodiments, the glycopyrronium compound is present at a concentration of about 1, 2, 3, or 4% (w/w). In some embodiments, the glycopyrronium compound is present at a concentration of about 3% (w/w). In an embodiment, the topical dosage form comprises about 70-105 mg of glycopyrronium compound. In an embodiment, the topical dosage form comprises about 66 mg of glycopyrronium base compound. In an embodiment, the topical dosage form comprises about 105 mg of glycopyrronium tosylate monohydrate. In some embodiments, the dosage form comprises more than one dose. In some embodiments the pharmaceutical composition is contained in a container or delivery device to apply multiple applications of said pharmaceutical composition. In some embodiments, the pharmaceutical composition is contained in a container or delivery device comprising about 10 g to about 50 g of solution. In some embodiments, the pharmaceutical composition is a stick comprising about 15 g to about 75 g of composition, for instance about 73 g of composition.

In an embodiment, the alcohol:water ratio of the topical dosage form is selected over the range of 50:50 to 70:30, preferably over the range of 53:47 to 58:42. In an embodiment, the alcohol:water ratio of the composition is selected over the range of 45:50 to 70:30. In an embodiment, the buffering agent is about 0.2 to 0.5% of the topical dosage form. In an embodiment, the buffering agent of the topical dosage form is citric acid/sodium citrate. In an embodiment, the pH of the topical dosage form is selected over the range of 4.0 to 5.0. In an embodiment, the pH of the topical dosage form is about 4.5. In certain embodiments, the pharmaceutical composition comprises about 105 mg threo glycopyrronium tosylate monohydrate, citric acid, sodium citrate, ethanol, and water at a pH of about 4.5. In certain embodiments, the pharmaceutical composition comprises about 66 mg threo glycopyrronium base compound, citric acid, sodium citrate, ethanol, and water at a pH of about 4.5.

In some embodiments, multiple doses of the pharmaceutical composition, e.g., providing up to about 250 mg, up to about 500 mg, up to about 1 gram, up to about 5 grams, up to about 10 grams, up to about 20 grams, up to about 30 grams, up to about 50 grams, up to about 100 grams, of glycopyrronium base compound in a applicator or delivery device to provide multiple doses. In some embodiments, multiple doses of the pharmaceutical composition, e.g., about 10 mL to about 50 mL, about 10 mL to about 40 mL, about 10 mL to about 30 mL, or about 20 mL to about 20 mL of the pharmaceutical composition are contained in a applicator or delivery device to provide multiple doses. In some embodiments, the applicator or delivery device can deliver up to 5 doses, up to 10 doses, up to 25 doses, up to 50 doses.

In certain embodiments, the pharmaceutical composition comprises a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate, about 0.15% by weight anhydrous citric acid, about 0.06% sodium citrate dihydrate by weight, between about 57 to about 59.5% by weight of dehydrated ethanol, and the balance as water. In some embodiments, the pharmaceutical composition comprises non-dehydrated alcohol with the alcohol:water ratio of the composition selected over the range of about 55% to about 65%. In some embodiments, the pharmaceutical composition comprises dehydrated alcohol with the alcohol:water ratio of the composition selected over the range of 45:50 to 70:30. In some embodiments, the pharmaceutical composition comprises non-dehydrated alcohol with the alcohol: water ratio of the composition selected over the range of 45:50 to 70:30.

In certain embodiments, the pharmaceutical composition comprises about 2.8 grams of a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate, about 0.15% by weight anhydrous citric acid, about 0.06% sodium citrate dihydrate by weight, between about 57 to about 59.5% by weight of dehydrated ethanol, and the balance as water. In certain embodiments, the amount of dehydrated ethanol is from about 45% to about 60%, from about 45% to about 55%, or from about 45% to about 50%.

In certain embodiments, the pharmaceutical composition is provided as a wipe or cloth moistened with the pharmaceutical formulation. The wipe or cloth can be about 100% polypropylene. The wipe or cloth can be contained in a pouch, for instance a laminated foil pouch. In some embodiments, the pharmaceutical composition is provided in a container, applicator, or delivery device for multiple applications. In some embodiments the pharmaceutical composition is provided in a stick, bottle, roll-on, or spray apparatus to deliver multiple doses.

D. Compounds and Pharmaceutical Compositions

Also provided herein are kits for use in the methods provided herein. In some embodiments, the kit comprises a pharmaceutical composition comprising a compound described herein and a material for occluding the skin. In certain embodiments, the material is a cotton glove. In certain embodiments, the material is a nitrile glove. In certain embodiments, the material is a cotton sock. In certain embodiments, the material is a nitrile sock. The kit can further comprise instructions, for instance for administration, occlusion, and/or monitoring. The kit can further comprise materials for an assessment, e.g. an HDSS assessment or an ASDD assessment modified as described herein, or both.

In some embodiments, the kit further comprises packaging. In some aspects, this packaging includes a container suitable for holding a pharmaceutical composition. The container can be made of any suitable material. Suitable materials include, for example, glass, plastic paper, laminates, and the like.

EXAMPLES

Unless otherwise stated, chemical reagents were purchased from commercially available sources.

Reagents used herein are available from commercial vendors and were purchased from commercially available sources unless specified herein otherwise or unless the preparation of the reagent(s) is/are described herein.

Example 1

Palmar hyperhidrosis patients (n=30) are evaluated in a randomized, double-blind, vehicle-controlled study. A glycopyrronium tosylate formulation, and optionally, a vehicle control, is administered to the palmar skin of each patient by vigorous, thorough application. The palms of each patient are occluded with cotton or nitrile gloves overnight. Application is repeated daily or twice daily for four weeks.

After four, eight, or twelve weeks, results are measured by standard questionnaires. For example, the Hyperhidrosis Disease Severity Scale (HDSS) utilizes a single question with a score of 1 to 4 to assess hyperhidrosis. See Solish et al., *Dermatol. Surg.,* 2007, 33:908-923. Alternatively, the Axillary Sweating Daily Diary (ASDD) can be adapted for palmar assessment. Nelson et al., 2019*, J. Patient Rep Outcomes* 3(1):59.

Example 2

Plantar hyperhidrosis patients (n=30) are evaluated in a randomized, double-blind study. A glycopyrronium tosylate formulation is administered to the plantar skin of each patient by vigorous, thorough application. The feet of each patient are occluded with cotton or nitrile socks overnight. Application is repeated daily or twice daily for four weeks.

After four, eight, or twelve weeks, results are measured by standard questionnaires such as HDSS or ASDD, adapted for plantar hyperhidrosis.

Example 3

Figure 1:
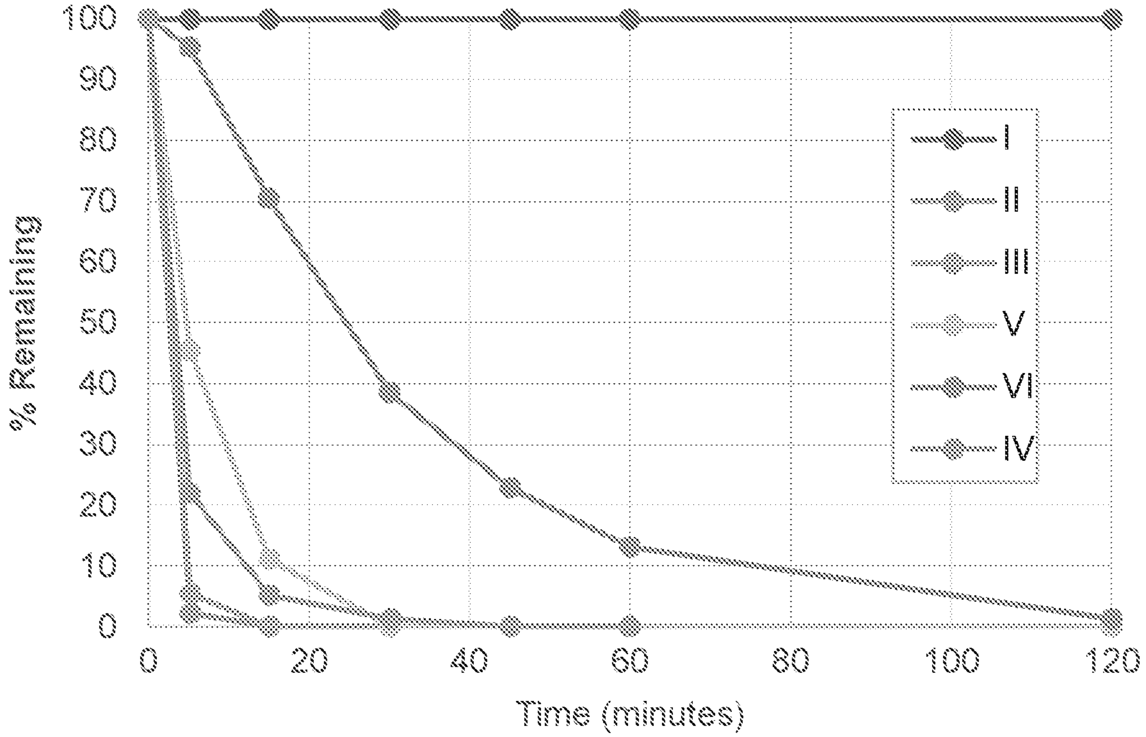
FIG. 1 depicts the rates of plasma inactivation of the formulations in an in vitro assay.

Stability of Formulations I-VI was assessed after 5, 15, 30, 45, 60 and 120 minutes incubation in plasma at. As shown in FIG. 1, Formulation 1 remained stable after 120 minutes incubation. In contrast, formulations II-V showed rapid degradation, with 100% degradation within 30 minutes. Formulation VI showed 60% degradation at 30 minutes, and >85% degradation at 60 minutes, and 100% degradation at 120 minutes.

Example 4

Formulations I-VI were assayed using the Epiderm® Skin Irritation assay. Briefly, the assay is directed to in vitro skin irritation testing of chemicals, including cosmetic and pharmaceutical ingredients. The EpiDerm SIT utilizes the 3D in vitro reconstructed human epidermal (RHE) model EpiDerm. The procedure discriminates between irritants of GHS category 2 and non-irritants. In the current example, the test was performed over the course of a 4 day time period, consisting of pre-incubation, 60 minute exposure, 42 hour post-incubation and MTT viability assay. After tissue receipt and overnight pre-incubation (Day 0), tissues were topically exposed to Formulations I-VI (Day 1). Three tissues were used for each test chemical, as well as for the positive (5% aq. SDS solution), and negative (DPBS) controls. Chemical exposure lasted for 60 minutes, 35 min of which the tissues were kept in an incubator at 37° C. The test substances were then removed from the tissue surface by an extensive washing procedure. The tissue inserts were blotted and transferred to fresh medium. After a 24 hr incubation period (Day 2), the medium was exchanged. After the medium exchange, tissues were incubated for an additional 18 hours. At the end of the entire 42 h post-incubation (day 3), the tissues were transferred into yellow MTT solution and incubated for 3 hours. The resultant purple-blue formazan salt, formed mainly by mitochondrial metabolism, was extracted for 2 hours using isopropanol. The optical density of the extracted formazan was determined using a spectrophotometer. A chemical is classified as an irritant if the tissue viability relative to the negative control treated tissues is reduced below 50%. As seen in FIGS. 2 and 3, using the Epiderm®, Formulations I-VI, Formulations I and VI were found to be moderate-mildly irritating, Formulations II and III were found to be very mild to non-irritating, and Formulations IV and V were found to be non-irritating.

Example 5

Formulations I-VI were subjected to skin/tissue permeation testing using MedFlux technology.

Human skin from 3 skin donors was mounted between the donor and receptor compartment of the MedFlux-HT™ diffusion cell (with an exposed dosing surface area of ~1 $cm^2$). Skin was dermatomed to a thickness of approx. 500 μm. The skin was dosed with approximately 10 mg of each of Formulations VI, V, I, III, and II to achieve a dose of ~10 $mg/cm^2$. A receptor solution flow through cell (no skin or formulation) and a blank cell (skin, no formulation) was also set up. The pump of the MedFlux system was adjusted to maintain a continuous receptor solution flow-rate of approximately 10 μL/min (600 μL/hr) directly under the skin. Receptor solution was automatically collected into a 96-well plate at 2 hour intervals over the course of 24 h and analysed using a single LC-MS/MS analytical method. Following 24 h, the residual formulation was removed from the surface of the skin and then the skin surface was tape stripped up to 5 times to remove residual formulation and the top of the skin surface layers (Stratum Corneum). The epidermis was then heat-separated from the dermis by placing the skin into an incubator at 60° C. for 2 min, followed by manual separation using forceps. The amount of each drug delivered to epidermis and dermis was then determined by LC-MS/MS.

The mean cumulative amount of API ($ng/cm^2$) delivered to the receptor solution 24 h post-application of the 5 formulations (FIG. 4A) and the bottom 3 formulations (FIG. 4B). Data points represent the cumulative amount of API from 5 replicates and 3 donors (n=11-15). Error bars represent standard error of the mean. Formulations are listed in rank order as shown in FIG. 5. Outliers were excluded using either the Dixon Outlier Test or visual inspection. Mean cumulative amount of API (ng) recovered from epidermis and dermis 24 h post-application of 5 formulations. Bars represent the cumulative amount of API from 5 replicates and 3 donors (n=11-15). Error bars represent standard error of the mean. Outliers were excluded using either the Dixon Outlier Test or visual inspection.

For epidermis-based assays, tertiary amines (Formulations VI and V) delivered 3 fold more API ($p<0.05$) compared to the quaternary amines (Formulations I, III, and II). All quaternary amines were statistically the same.

For dermis-based assays, Tertiary amines (Formulations VI and V) delivered 4 fold greater ($p<0.05$) concentrations of API compared to the quaternary amines (Formulations I, III, and II). All other formulations were statistically the same.

For receptor solution-based assays, i.e., wherein delivery is greater than 500 μm deep, where sweat glands are, the tertiary amines (Formulations VI and V) delivered 25 fold more API ($p<0.05$) compared to the quaternary amines (Formulations I, III, and II).

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A method for palmar or plantar administration of a compound to a subject in need thereof comprising the steps of:

a. administering to the palmar or plantar skin of the subject an anticholinergic compound; and b. occluding the palmar or plantar skin of the subject for a time sufficient for the compound to have an anticholinergic effect on the palmar or plantar skin of the subject, wherein the anticholinergic compound is threo glycopyrronium tosylate monohydrate, sofpironium bromide, or a compound selected from II, III, IV, V, or VI:

II

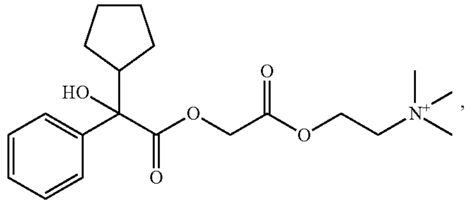

III

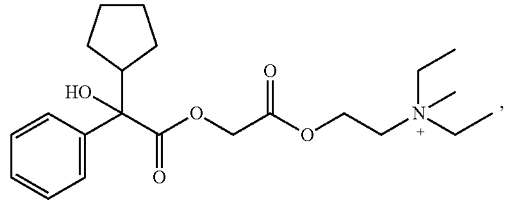

IV

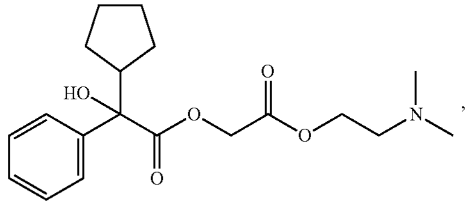

-continued

V

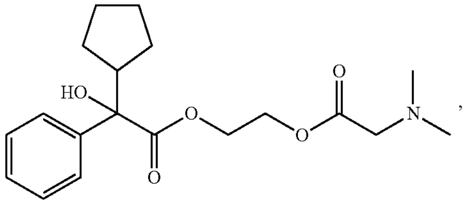

VI

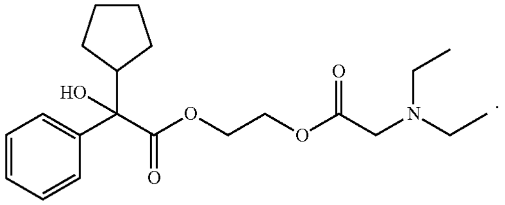

2. The method of claim 1, wherein the occluding comprises applying a material to the skin.

3. The method of claim 2, wherein the material is selected from cotton, nitrile, polyethylene, latex, butyl rubber, neoprene, wool, rayon, acrylic fiber, and combinations thereof.

4. The method of claim 1, wherein the occluding comprises applying a glove or sock to the skin of the subject.

5. The method of claim 1, wherein the occluding comprises applying a cotton glove or sock to the skin of the subject.

6. The method of claim 1, wherein the occluding comprises applying a nitrile glove or sock to the skin of the subject.

7. The method of claim 1, wherein the anticholinergic compound is in a pharmaceutical composition comprising the compound and a pharmaceutically acceptable carrier, excipient, or diluent.

8. The method of claim 1 wherein the pharmaceutical composition is formulated as a topical composition.

9. The method of claim 1, wherein the dose of the compound is from 0.1 to about 500 mg, from about 0.1 to about 100 mg, from 0.1 to about 50 mg, from 0.1 to about 40 mg, or from 0.1 to about 30 mg.

10. The method of claim 1, for treating hyperhidrosis wherein the subject is in need thereof.

11. The method of claim 1, wherein the subject is a mammal.

12. The method of claim 10, wherein the subject is a human.

13. The method of claim 12 for treating palmar or plantar hyperhidrosis, wherein the human has palmar or plantar hyperhidrosis.

14. The method of claim 1, wherein the compound is sofpironium bromide.

15. The method of claim 1, wherein the compound is threo glycopyrronium tosylate monohydrate.

16. The method of claim 15, wherein administering to the palmar or plantar skin, comprises a dose from about 0.1 mg to about 105 mg of threo glycopyrronium tosylate monohydrate.

17. The method of claim 15, wherein the administration comprises applying the compound to the palmar or plantar skin of the subject for 1 to 10 minutes.

18. The method of claim 17, wherein the administering comprises the compound in a topical formulation or a wipe or cloth comprising a solution of the compound.

19. The method of claim 16, wherein administering comprises 2 to 3 doses per day.

20. The method of claim 16, wherein administering comprises a dose every day or twice a day for 1 to 4 weeks.

21. The method of claim 15, wherein occluding the palmar or plantar skin of the subject comprises occluding the palms and/or feet of the subject with cotton or nitrile gloves and/or socks, respectively.

22. The method of claim 21, wherein occluding with gloves and/or socks occurs for about 1 to 8 hours or overnight.

23. The method of claim 1, wherein the compound is a compound of formula II:

II

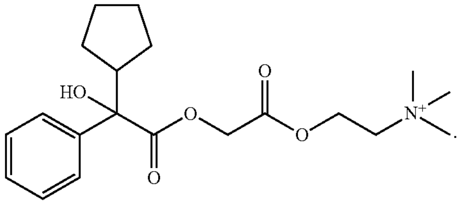

24. The method of claim 1, wherein the compound is a compound of formula III:

III

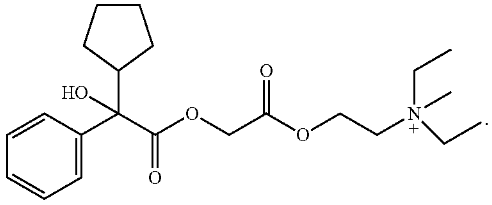

25. The method of claim 1, wherein the compound is a compound of formula IV:

IV

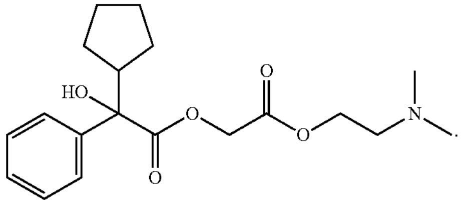

26. The method of claim 1, wherein the compound is a compound of formula V:

V

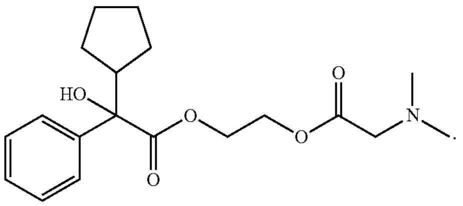

27. The method of claim 1, wherein the compound is a compound of formula VI:
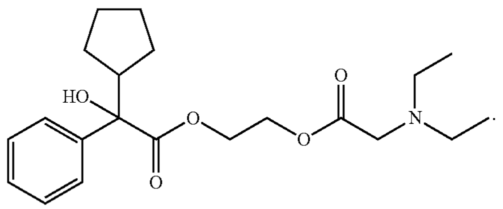
VI
* * * * *